United States Patent [19]

Beldock et al.

[11] Patent Number: 5,648,398
[45] Date of Patent: Jul. 15, 1997

[54] INSECT REPELLENT LOTIONS AND SPRAYS

[75] Inventors: Donald T. Beldock, New York, N.Y.;
John A. Beldock, Washington, D.C.

[73] Assignee: Primavera Laboratories, Inc., Rye, N.Y.

[21] Appl. No.: 298,839

[22] Filed: Aug. 31, 1994

Related U.S. Application Data

[62] Division of Ser. No. 37,260, Mar. 26, 1993, Pat. No. 5,346,922, which is a division of Ser. No. 905,166, Jun. 24, 1992, Pat. No. 5,227,406, which is a continuation of Ser. No. 506,471, Apr. 9, 1990, abandoned.

[51] Int. Cl.$^6$ .......................... A01N 31/02; A01N 31/04; A01N 31/06
[52] U.S. Cl. .......................... 514/703; 514/729; 514/739; 514/919; 424/195.1; 424/DIG. 10
[58] Field of Search .......................... 514/703, 729, 514/739, 919; 424/195.1, DIG. 10

[56] References Cited

U.S. PATENT DOCUMENTS

| | | | |
|---|---|---|---|
| 3,988,432 | 10/1976 | Stertenkemp | 424/49 |
| 4,193,986 | 3/1980 | Cox | 424/28 |
| 4,478,853 | 10/1984 | Chaussee | 514/777 |
| 4,774,081 | 9/1988 | Flashinski et al. | 514/919 |
| 4,829,092 | 5/1989 | Nelson et al. | 514/738 |
| 5,521,165 | 5/1996 | Warren et al. | 514/64 |

FOREIGN PATENT DOCUMENTS

| | | |
|---|---|---|
| 1230826 | 12/1987 | Canada . |
| 0275085 | 7/1988 | European Pat. Off. . |
| A855176 | 5/1940 | France . |
| 2622103 | 4/1989 | France . |
| 267202 | 3/1990 | Japan . |

OTHER PUBLICATIONS

"Die Insektide, Chemie, Wirkungsweise und Toxicitant", Dr Werner Perkow, 1968.
The Merch Index, 11th Edition, Rahway, NJ, Merck & Co., Inc. 1989, pp. 1072–1074.
Derwent Abstract Accession No. 76–19329X, Abstracting JP 51–9729 (Jan. 26, 1976).
Chemical Abstracts 112:164746e (1990).
Chemical Abstracts 104: 30390k (1986).
Chemical Abstracts 113: 110945w (1990).
Chemical Abstracts 105:204742Q (1986).
The Merck Index, 10th Edition Rahway, NJ, Merck & Co, Inc. 1983 pp. 332, 629, 1180–1181 and 1312.
"Chemicals Evaluated as Insecticides and Repellents at Orlando, FL," W.V. King, US Dept. of Agriculture, Agricultural Handbook No. 69, 1954, pp. 13–16 and 246.

*Primary Examiner*—John Pak
*Attorney, Agent, or Firm*—David P. Gordon

[57] ABSTRACT

An insect repellent is provided and includes terpineol, citronella, and one or both of rhodinol extra and geraniol as actives provided in a conveying medium. The actives are used in small percentages, e.g. as little as 0.01%, preferably at between 0.05% and 0.08%, and preferably less than 1%, yet are synergistically efficacious, particularly against ticks carrying Lyme disease. The conveying medium can be a cosmetic moisturizer lotion, with or without a sun screen. For a spray, the conveying medium can be water or alcohol based. An attractive fragrance is preferably provided as approximately 0.4% of the insect repellent. The lotion or spray is safely applied in liberal quantities to humans and animals without unpleasant side effects such as stinging.

7 Claims, No Drawings

INSECT REPELLENT LOTIONS AND SPRAYS

This is a divisional of application Ser. No. 08/037,260 filed on Mar. 26, 1993, now U.S. Pat. No. 5,346,922, which in turn is a divisional of Ser. No. 07/905,166 filed on Jun. 24, 1992, now U.S. Pat. No. 5,227,466, which in turn is a continuation of Ser. No. 07/506,471 filed Apr. 9, 1990 and now abandoned.

BACKGROUND OF THE INVENTION

The present invention relates generally to insect repellents in lotion and spray form. More particularly, the present invention relates to insect repellents for humans and animals which are particularly efficacious in repelling ticks carrying Lyme disease, as well as biting flies and triatomes (Chagas bugs). For purposes herein, the term "insect" is to be understood in its broadest sense to include ticks, Chages bugs, biting flies, etc.

Insects have long been carriers and spreaders of diseases as they not only feed on animals, but on humans as well. In North America, mosquitoes, ticks, and black flies are the three major groups of arthropods pestiforous to humans. While black flies and mosquitoes in North America are primarily a nuisance, a tick bite can be more serious. In particular, significant attention in the northeast United States recently has been focused upon the Lyme disease ticks (*ixodes damini*) which have spread in geographical area as well as in number, and which carry the potentially debilitating Lyme disease. Similarly, in warmer climates such as Latin America, a serious and potentially fatal malady known as Chagas' disease are carried by triatomes (Chagas bugs) which are active at night and feed on people as they sleep. In Africa, mosquitoes carry malaria.

In an attempt to repel insects, people have turned to widely marketed lotions and sprays (e.g. Cutters, Deep-Woods Off, and Tick Garde) which contain N,N-diethyl-m-toluamide (DEET) as their active ingredient. While DEET is an effective repellent, it is not particularly pleasing in smell, it stings when applied, and its use has a number of harmful side-effects to humans. DEET is injurious to eyes, mucous membranes, and sensitive skin. In addition, because DEET is absorbed through the skin, toxic systemic reactions may result as well. For example, in August 1989, the New York State Department of Health investigated five reports of generalized seizures which were believed to be associated with the topical application of DEET. Other symptoms and maladies associated with repeated exposure to DEET have included irritability, confusion, insomnia, encephalopathy, and coma. As a result, cautionary statements regarding use of DEET have been issued by the Centers for Disease Control and the states of New York, Connecticut, New Jersey, and Utah.

The potential hazards of using a product with DEET as an active ingredient suggests that there exists a great need for a comparably repellent product that is not dangerous to its users. This is particularly true in light of the dramatic increase in the incidences of Lyme tick bites.

SUMMARY OF THE INVENTION

It is therefore an object of the invention to provide an effective insect repellent which is safe to use.

It is another object of the invention to provide an effective insect repellent which has an attractive fragrance.

It is a further object of the invention to provide an effective insect repellent which can be used with different mediums.

It is yet another object of the invention to provide an insect repellent which effectively repels Lyme disease ticks, mosquitoes, and other insects.

It is also a further object of the invention to provide a safe, effective insect repellent which can be applied liberally to the face, skin, and clothes of a person.

It is even another object of the invention to provide an insect repellent which is safe and effective for animals.

In accord with the objects of the invention, a first embodiment of an insect repellent is provided and comprises a medium to which active ingredients of at least 0.01% terpineol, at least 0.01% citronella, and at least 0.01% geraniol are added, wherein the listed percentages are weight percentages. In a second embodiment, at least 0.01% rhodinol extra is added to the three other actives. In a third embodiment, a medium is provided with at least 0.01% terpineol, at least 0.01% citronella, and at least 0.01% rhodinol extra. In the preferred embodiment, a cosmetic moisturizing lotion, spray, or cream medium is provided, to which 0.06% terpineol, 0.05% citronella, 0.08% rhodinol extra, and 0.06% geraniol are added, as well as 0.4% fragrance formula #HB-728 of Shaw Mudge & Co. If desired, the actives may be provided in greater quantities, although it is believed that little is gained by providing the actives at concentrations above 1%. The embodiments as summarized have insect repellency efficacy well beyond what would be expected, as the combination of actives has a synergistic effect.

According to other preferred aspects of the invention, the actives may be added to a sun screen lotion of desired SPF level to provide a multipurpose lotion, or to water or alcohol to provide an insect repellent spray.

Other objects and advantages of the present invention will become evident upon reference to the detailed description which follows.

DETAILED DESCRIPTION OF THE PREFERRED EMBODIMENTS

According to the preferred embodiment, an insect repellent is provided which comprises a cosmetic moisturizer lotion base to which 0.06% terpineol, 0.05% citronella, 0.08% rhodinol extra, and 0.06% geraniol are added, as well as 0.4% fragrance formula #HB-728 of Shaw Mudge & Co. (all percentages being weight percentages). The provided insect repellent (hereinafter referred to as TREO) is safe to use, has excellent repellency characteristics, and has a pleasant smell.

TREO was tested for efficacy against DEET products in several areas of North America and Central America in different habitats, at different times of year, and against a wide variety of biting arthropods, including disease vectors. Several different human subjects were used to reduce any effects of inter-individual differences in attractiveness to biting arthropods. In each trial with mosquitoes or other biting flies, each human subject had one arm treated with a repellent (DEET or TREO) and the other untreated, permitting simultaneous testing. Bites were counted on each arm below the shoulder. In trials with ticks on Nantucket, conventional 2' by 2' flannel flags were treated with TREO, a DEET product, or were left untreated. These flags were passed through vegetation harboring ticks.

Table 1 summarizes the results of the five main investigations:

TABLE 1

Repellency of TREO compared to products
containing 35-38 & DEET and to untreated controls

| Arthropod/Sites | Treatment | | |
|---|---|---|---|
| | TREO | DEET | Untreated |
| Mosquito (FL & TX)[1] | 5 | 3 | 170 |
| Mosquito (Utah)[1] | 16 | 3 | 451 |
| Ticks (Mass)[2] | 0 | 0 | 20 |
| Ticks (laboratory)[3] | 0.3 | 1.25 | 4.0 |
| Black Flies (Belize)[1] | 0 | 0 | 55 |

[1]Numbers of bites per treatment
[2]Numbers of ticks clinging to cloth
[3]Numbers of ticks crossing a repellent barrier per minute From Table 1 it is seen that TREO proved to be an excellent repellent against all arthropods tested. In tests with mosquitoes in winter and spring in Florida and Texas, both TREO and a DEET product reduced biting rates by approximately 97–98%. In summer tests in Utah, the DEET product was marginally more effective against the marshlandmosquito Aedes dorsalis, but the products were equally effective against the common urban and suburban pest Cluex tarsalis, the vector of Western Equine Encephalitis. In Belize, TREO was an absolute repellent against simuliid black files, which are vectors of river blindness, one of the ten most important arthropod borne diseases in the world. Also, in unquantified trials not shown in Table 1, TREO provided extreme protection against mosquitoes and ceraptopogonid black flies (No-see-ums) in Belize.

The Massachusetts tick test of Table 1 was conducted on Nantucket Island, in the month of October when approximately sixty percent of the ticks on Nantucket carry Lyme disease. Ticks were collected using the conventional technique of "flagging": 2'×2' sheets of white flannel cloth were tacked to wooden dowels, and then swept across the tips of low vegetation harboring active ticks along hiking trails, deer trails, and dirt roads. The results of the test show that TREO was completely effective in repelling the Ixodes damini tick.

Because it is known that people wearing a DEET product repellent have been bitten by ticks, a laboratory study with ticks was conducted. The ticks were placed in the centers of filter paper disks either left untreated or ringed by TREO or a DEET product, and the rate at which the ticks crossed the barrier (an untreated or treated ring) monitored. The laboratory test showed TREO to be a more repellent barrier to ticks than the DEET product. Ticks ringed with the DEET products lifted their bodies away from the repellent, but still crossed the treated area relatively quickly, while ticks ringed with TREO all turned back from the barrier at least once and required several attempts before crossing the barrier. Thus, TREO was found to be a true repellent of ticks as not only did TREO discourage initial contact with ticks (the Massachusetts flag test), but also reduced the probability that a tick which might adhere to clothing treated with TREO would climb past a TREO barrier to find an attachment site for blood-feeding. In nature, rather than in the laboratory, it is believed that ticks would simply turn and walk off or drop off a person rather than repeatedly attempting to cross the barrier.

As aforementioned, the preferred embodiment of TREO contains four actives in amounts between 0.05 and 0.08 weight percent of a lotion. Testing has shown that the actives alone in concentrations of up to one percent are not as effective as the combined actives in the smaller percentages. Also, subcombinations of the actives in the small amounts proved to be as or nearly as effective as individual actives in the larger concentrations. In particular, Table 2 shows relative alighting percentages of mosquitoes in field and laboratory tests where human arms and paper were treated with the single active, and combinations of the actives in different percentages. The alighting percent should be interpreted as 100% minus the percentage of mosquitoes which turned away from the treated arm or paper.

TABLE 2

Percent of mosquitoes resting on paper or arms
treated single constituent and combination of constituents

| Constituent | | | | |
|---|---|---|---|---|
| Terpineol | Citronella | Rhodinol Extra | Geraniol | Alighting % |
| 1% | — | — | — | 12% |
| — | 1% | — | — | 6% |
| — | — | 1% | — | 9% |
| — | — | — | 1% | 12% |
| 1% | 1% | 1% | — | 6% |
| 1% | 1% | 1% | 1% | 3% |
| .06% | .05% | .08% | .06% | 3% |
| .06% | .05% | .08% | | 12% |
| .06% | .05% | | .06% | 12% |

From Table 2, it is seen that the four constituent combination is as effective with weight percentages of between 0.05% and 0.08% as it is with weight percentages of 1%. Because increased percentages provide little or no advantages, it is preferable to limit each active in TREO to 1% of the lotion. Furthermore, it is believed that the four constituent combination has efficacy as an insect repellent in even lower percentages: each active being at 0.01% or higher. Also, as shown in Table 2, while not as effective as the four constituent combination, two different three constituent combinations do function as insect repellents. Thus, the combinations of terpineol, citronella, and geraniol, and terpineol, citronella, and rhodinol extra are believed to have synergistic efficacy where each active is provided in percentages of at least 0.01%.

Those skilled in the art will appreciate that the actives in TREO can be carried in different forms. One preferred form is a moisturizer lotion including one or more of glycerin, lanolin alcohol, aloe vera gel, sweet almond oil, propylene glycol, mineral oil, cetyl alcohol, cetyl acetate, and octyl palmitate, to which a fragrance is added. The preferred fragrance is formula #HB-728 of Shaw Mudge & Co., Stamford, Connecticut, which is added to comprise 0.4% of the moisturizer lotion. The preferred fragrance appears to mask the odor of the actives (which is generally unpleasant to humans) to the human sense of smell, while not adversely affecting the efficacy of the insect repellent to insects.

According to another preferred aspect of the invention, the TREO actives (or preferred subsets) are added to a sun screen lotion of desired SPF level containing actives such as octyl methoxycinnamate, benzophenon-3, or octyl salicylate, to provide a multipurpose lotion; i.e. a sunscreen; a tick/insect repellent; and a moisturizing cream.

In accord with another aspect of the invention, the TREO actives (or the preferred subsets) are added in the preferred percentages to a water or alcohol medium to provide an insect repellent spray. The spray is particularly useful for clothing, and either the spray or lotion can be used as an insect repellent for cats, dogs, cattle, sheep, and other animals.

There have been described herein insect repellents which incorporate three or more actives in small percentages into a conveying medium. While particular embodiments have been described, it is not intended that the invention be limited thereto, as it is intended that the invention be as broad in scope as the art will allow. Thus, while preferred percentages and ranges of actives were described, it will be appreciated that different relative percentages of the actives within those ranges could be utilized, although it is not known whether the resulting combination would be as efficacious as the preferred embodiment. Further, while preferred conveying mediums were described, other mediums including, but not limited to lotions, sprays, and creams could be utilized. In fact, other active ingredients for other purposes, such as suntanning, sunscreening, sun-blocking, etc. can be added to the lotions, sprays or creams. Also, while a certain fragrance was described as being used in a particular amount, other fragrances could be utilized, and different amounts of fragrance could be utilized although the other fragrances or different amounts might not mask the odor of the actives as well or as pleasantly as is done in the preferred embodiment. Therefore, it will be appreciated by those skilled in the art that yet other modifications could be made to the provided invention without deviating from its spirit and scope as so claimed.

I claim:

1. An insect repellent, comprising:
   a) a conveying medium constituting up to 99.96% of the insect repellent;
   b) between 0.01% and 1% terpineol;
   c) between 0.01% and 1% citronella;
   d) between 0.01% and 1% rhodinol extra;
   e) between 0.01% and 1% geraniol; and
   f) a fragrance which substantially masks the odor of said terpineol, said citronella, said rhodinol extra, and said geraniol to humans, but does not substantially reduce the repellency of said insect repellent to insects,
   wherein all listed percentages (%) are weight percentages.

2. An insect repellent according to claim 1, wherein:
   said fragrance is substantially 0.4% by weight of said insect repellent.

3. An insect repellent, comprising:
   a) a conveying medium constituting up to 99.97% of the insect repellent;
   b) between 0.01% and 1% terpineol;
   c) between 0.01% and 1% citronella;
   d) between 0.01% and 1% geraniol; and
   e) a fragrance which substantially masks the odor of said terpineol, said citronella, and said geraniol to humans, but does substantially reduce the repellency of said insect repellent to insects,
   wherein all listed percentages (%) are weight percentages.

4. An insect repellent according to claim 3, wherein:
   said fragrance is substantially 0.4% by weight of said insect repellent.

5. An insect repellent according to claim 3, wherein:
   said conveying medium constitutes up to 99.96% of the insect repellent, and said insect repellent further comprises between 0.01% and 1% rhodinol extra
   wherein all listed percentages (%) are weight percentages.

6. An insect repellent, comprising:
   a) a conveying medium constituting up to 99.97% of the insect repellent;
   b) between 0.01% and 1% terpineol;
   c) between 0.01% and 1% citronella;
   d) between 0.01% and 1% rhodinol extra; and
   e) a fragrance which substantially masks the odor of said terpineol, said citronella, and said rhodinol extra to humans, but does substantially reduce the repellency of said insect repellent to insects,
   wherein all listed percentages (%) are weight percentages.

7. An insect repellent according to claim 6, wherein:
   said fragrance is substantially 0.4% by weight of said insect repellent.

* * * * *